United States Patent [19]
Zutler

[11] Patent Number: 5,265,749
[45] Date of Patent: Nov. 30, 1993

[54] CONTAINER

[75] Inventor: Michael B. Zutler, Woodbury, N.Y.

[73] Assignee: Marketing Congress, Inc., Plainview, N.Y.

[21] Appl. No.: 41,505

[22] Filed: Apr. 1, 1993

[51] Int. Cl.[5] ............................................. B65D 83/00
[52] U.S. Cl. ................................... 220/4.24; 220/4.25; 220/360; 220/366; 220/DIG. 27; 239/58
[58] Field of Search ................. 220/4.24, 4.25, 4.21, 220/366, 367, 360, DIG. 27; 237/58, 59

[56] References Cited

U.S. PATENT DOCUMENTS

| | | | |
|---|---|---|---|
| 216,831 | 6/1879 | Collings | 220/4.24 |
| 239,225 | 3/1881 | Claussen | 220/4.24 |
| 3,208,620 | 9/1965 | Herdering | 220/4.24 |
| 3,568,146 | 2/1971 | Arnolds | 220/4.24 |
| 3,983,658 | 10/1976 | de Sanz | 220/4.25 |
| 4,049,357 | 9/1977 | Hamisch, Jr. | 220/4.24 |

*Primary Examiner*—Joseph Man-Fu Moy
*Attorney, Agent, or Firm*—Grimes & Battersby

[57] ABSTRACT

A container wherein a top member and a base member are formed as identical units, e.g., from a common mold, and have interactive shapes that permit the top to be laid upon the bottom in a nesting, closed configuration, and rotated relative to the bottom to one or more open configurations with at least three points of engagement whereby the size of the openings therebetween are varied in the different open positions and allow for movement of ambient air therebetween. The top cover and base, formed with identical common interfacing areas, can be subsequently modified, e.g., decorative or ornamental components can be added to the other, non-interfacing areas. Additionally, a handle could be added to the top cover. A pedestal could be added to the base. In a preferred embodiment, each member has a curvilinear outer periphery. During such rotation, there is a concomitant upward or vertical motion of the top member away from the base member caused by the camming interaction of the interfacing outer periphery curvilinear portions of the top and base members. The members are returned to the closed position by continuing further rotation in the same direction or by reversing the direction of rotation of the top member relative to the base member. The two members can be separated and then returned to nesting engagement, the outer peripheries engaging and guiding relative movement of the two members as they are returned to the nested configuration.

12 Claims, 3 Drawing Sheets

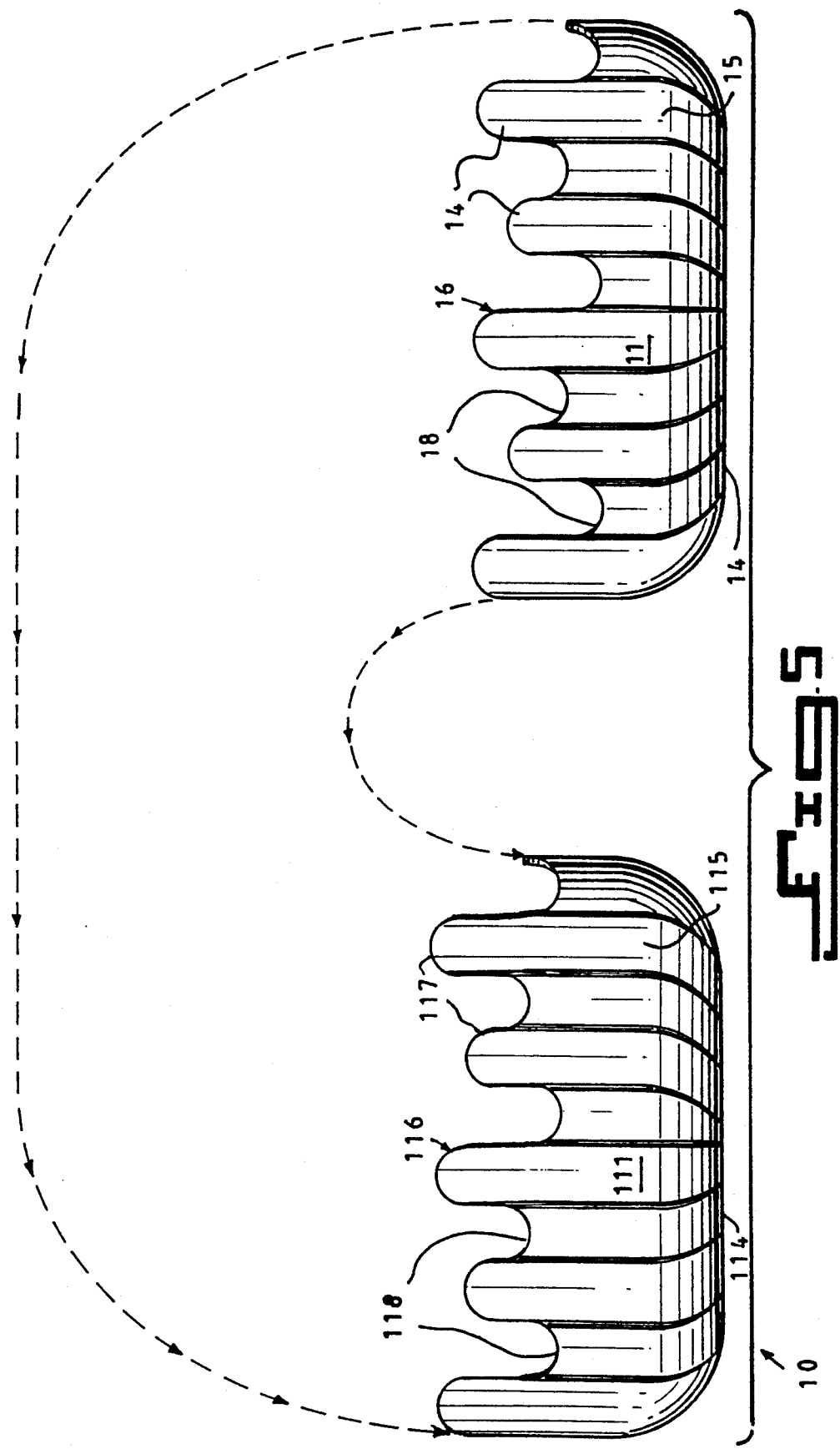

CONTAINER

BACKGROUND OF THE INVENTION

1. Field of the Invention

The present invention relates to a container wherein a top member and a base member are formed as identical units, e.g., from a common mold, and have interactive shapes that permit the top to be laid upon the bottom in a nesting, closed configuration, and rotated relative to the bottom to one or more open configurations with at least three points of engagement whereby the size of the openings therebetween are varied in the different open positions.

The top cover and base, formed with identical common interfacing areas, can be subsequently modified, e.g., decorative or ornamental components can be added to the other, non-interfacing areas. Additionally, a handle could be added to the top cover. A pedestal could be added to the base.

In the preferred embodiment, each member has a curvilinear outer periphery. The top member and the base member are designed to be nested relative to each other in either a closed, first position or one or more open, second positions. When they are in one of the open, second positions, spaces are formed between the top member and the base member, which spaces are designed to permit air-treating material in the container to be exposed to ambient air. To move the members from the closed to one of the open positions, the top member is rotated relative to the base member. During such rotation, there is a concomitant upward or vertical motion of the top member away from the base member caused by the camming interaction of the interfacing outer periphery curvilinear portions of the top and base members. The members are returned to the closed position by continuing further rotation of the top member relative to the base member in the same direction that brought about the opening, or by reversing the rotation of the top member relative to the base member until the members return to their original position of closed engagement. The camming outer periphery surfaces allow easy repositioning of the top member in nesting relation to the base member even after the top member has been completely removed, e.g., in order to permit replenishment of the air-treating material. As the two members are returned to nesting engagement, the outer peripheries will engage and guide further relative movement of the two members, i.e., movement of the top member vertically downward onto the base member, until the members seat relative to each other. The nature of the interaction of the outer peripheries when the top member is being replaced on the base member is such that only two degrees (i.e., "x" and "y" planes but not "z") of rotational freedom under such circumstances is permitted, thus limiting the chances of destructive banging of the members together.

2. Description of the Prior Art

A number of container designs have been developed whereby the contents of the container may be sealed off from the ambient air and thereafter opened to expose the contents to the ambient air. The contents of the containers are air treating materials which include volatile air treating components that are gradually introduced into the air such as air freshening, air deodorizing, air purifying, perfume, disinfection and insecticidal components. Typical prior art container designs are disclosed in U.S. Pat. Nos. 4,014,501; 4,372,490; 4,537,351; 4,382,548; 4,549,693; and 4,621,768.

Many prior art devices disclose containers whereby a top member is rotatably positioned on a bottom member. By rotating the top member relative to the bottom member either one or a plurality of apertures are opened thereby exposing the contents of the container to the ambient air. Although these devices overcome some of the deficiencies of the prior art containers, they suffer from a construction disadvantage in that the top member has a different configuration from the base member. In other words, to construct the container, it is necessary to mold the top member in a completely distinct mold from that used to mold the bottom member. This greatly increases the expense involved with constructing the container. In addition, it is necessary to closely monitor the construction of the top members and the base members to make sure that an equal quantity of members are being manufactured and to insure that manufacturing tolerances are accurate so that two different top and bottom members interact appropriately without problems.

Some prior art devices are also unsatisfactory because they require two hands to operate, i.e., to make adjustments. Others are unsatisfactory because they require a period of learning to use. Others do not permit easy replenishment of the air treatment material. Others, because of various mechanical requirements, impose design limitations which are not conducive to product aesthetics.

The LeCaire, Jr. et al. Patent No. 4,372,490 discloses a container wherein the base and top members are matching pieces made from a common mold. However, the nesting features are complex and do not simply and effectively accomplish the goals of allowing multiple stages o opening and controlled relative movement, including during complete disengagement and re-engagement of the two members. Neither does this design result in an acceptable container from an aesthetic standpoint nor permit removal of the top for replenishment of the material in the container.

SUMMARY OF THE INVENTION

Accordingly, it is a primary object of the present invention to provide a container wherein the top member and the base member are identical elements constructed from a single mold.

Another object of the present invention is to provide a container formed with identical interfacing areas that may have different design or aesthetic areas beyond the interface areas.

Another object of the present invention is to provide a container wherein the top member and the base member may be nested together in order to form an operative container which may be closed or opened.

A still further object of the present invention is to provide a container which is simple in construction and operation and at the same time attractive in appearance.

A further object of the present invention is to provide a top member and a base member which include outwardly projecting outer peripheries which mate with each other so that the top member may be reciprocated outwardly from the base member thereby defining air passages therebetween and inwardly to close and seal the container.

A still further object of the present invention is to provide a container wherein a top member and a base member are formed as identical units, e.g., from a common mold, and have interactive shapes that permit the top to be laid upon the bottom in a nesting, closed configuration, and rotated relative to the bottom to one or more open configurations with at least three points of engagement whereby the size of the openings therebetween are varied in the different open positions.

A still further object of the invention is to provide outer peripheries which are curvilinear in shape so as to permit smooth rotation of the two members relative to each other and indexing of the two peripheries relative to each other to adjust the positioning of said top member relative to said base member in a plurality of various positions to define different size air passages.

An additional object of the invention is to provide outer peripheries which are scalloped shaped in design so as to achieve the desired smooth rotation and indexing in an extremely, aesthetically attractive container.

These and other objects have been fulfilled in the present invention by providing a top member which is constructed in an identical configuration to the base member. The top member and base member each include a outer periphery that matingly engages the outer periphery of the other in a closed position and in one or more open positions. In the closed position, the outer peripheries are in complete engagement along their entire length. In the open positions, the outer peripheries are only in engagement along certain select portions of their length, in particular, along at least three distinct points of their lengths, and interspersed between those engaging portions are other non-engaging portions, which define air passages therebetween. A quantity of air-treating material is positioned between the top member and the base member and is normally positioned within the base member. In the open position, the top member is slightly rotated relative to the base member to shift the top member upwardly away from the base member. The outer peripheries can be curvilinear in shape, in which case such upward movement upon rotation of the top member is due to the camming interaction between the outer peripheries.

BRIEF DESCRIPTION OF THE DRAWINGS

The objects of the present invention and the attendant advantages thereof will become more readily apparent by reference to the following drawings wherein:

FIG. 5 is a side view of the top and base members of the container according to the present invention, disengaged from each other and laid side by side.

DETAILED DESCRIPTION OF THE PREFERRED EMBODIMENTS

Figure 1:
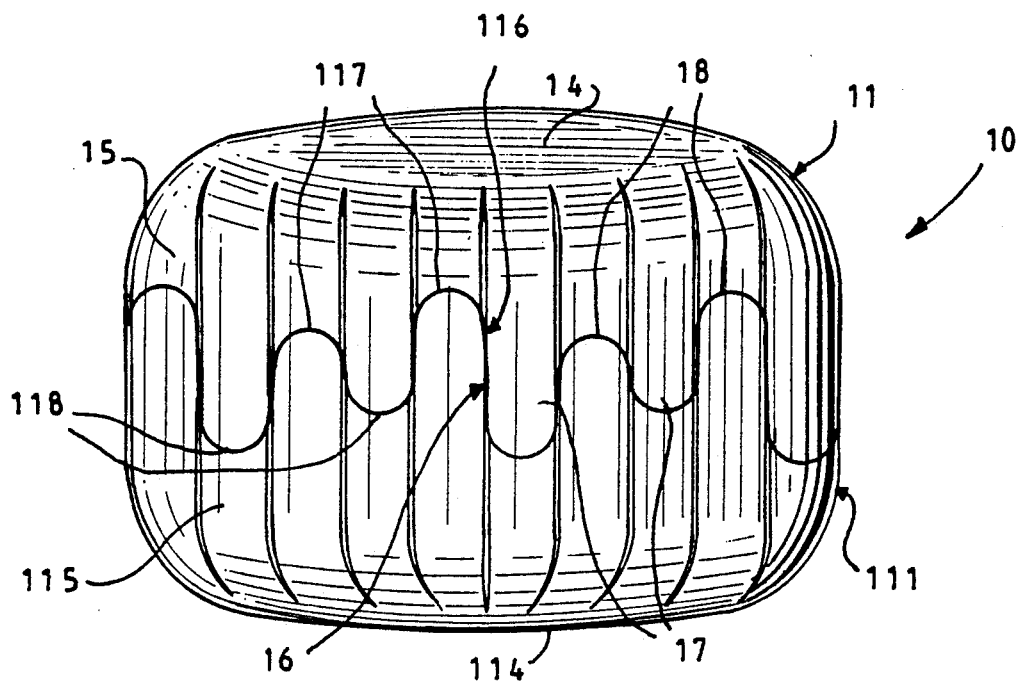
FIG. 1 is a side perspective view illustrating a preferred embodiment of the container according to the present invention in a closed position.

Referring in detail to FIG. 1, there is illustrated a container 10 shown in the closed position. The container 10 includes a top member or housing section 11 which is identical in construction to a base member or housing section 111, i.e., the top member 11 and the base member 111 have the identical shape, having been made from the same mold. The top member 11 includes a flat upper surface 14 and a side wall 15. The side wall 15 includes a curvilinear outer periphery or edge 16 that, in the preferred embodiment shown, is scallop shaped. The periphery 16 is defined by fingers 17 and recesses 18 which are, at the same time, both functional and decorative.

Similarly, the base member 111 includes a flat lower surface 114 and a side wall 115 which includes a curvilinear outer periphery or edge 116 that, in the preferred embodiment shown, is scallop shaped. The periphery 116 is defined by fingers 117 and recesses 118 that correspond respectively with the fingers 17 and recesses 18 of the top member 11.

The fingers 17 and 117 ar designed to mate with each of the recesses 118 and 18, respectively.

As shown in FIG. 1, the outer periphery 16 of the top member 11 engages the outer periphery 116 of the base member 111 when the container is in the first, closed position to close the interior of the container form the outside air. As discussed hereinbelow, the embodiment of the container 10 shown has a curvilinear shape whereby it repeats after every two fingers and two recesses.

In alternative embodiments, there could be repetitive sequences of fingers and recesses, accomplished by inserting fingers in between the two fingers shown of varying progressive sizes between the size of the small finger and the size of the larger finger and by inserting matching recesses in between the two recesses shown of varying progressive depths between the depth of the smaller recess and the depth of the larger recess. This would afford additional opened positions which the container can be rotated to in order to selectively control the release of the air treatment material. The greater the number of fingers and recesses, the greater the number of possible opened positions. Adding additional numbers of fingers and recesses permits more refined selection of the degree of material being released into the air.

Figure 2:
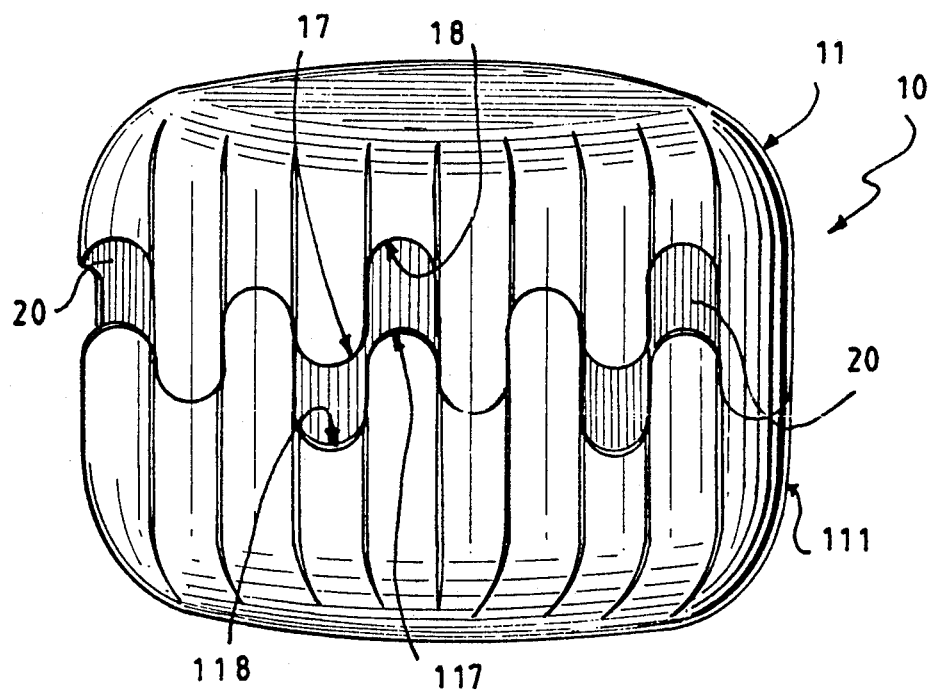
FIG. 2 is a side perspective view of the container according to the present invention illustrating the container in an open position.

Referring in detail to FIG. 2, the container 10 is illustrated in the open position. Like numerals in FIG. 2 represent the same elements as previously discussed with respect to FIG. 1. In the open position shown, the total sealing engagement of 16 and 116 has been discontinued. As a result of rotational motion of the top member 11 relative to the base member 111, a plurality of spaced portions 20 have been created between the top member 11 and the base member 111.

Figure 3:
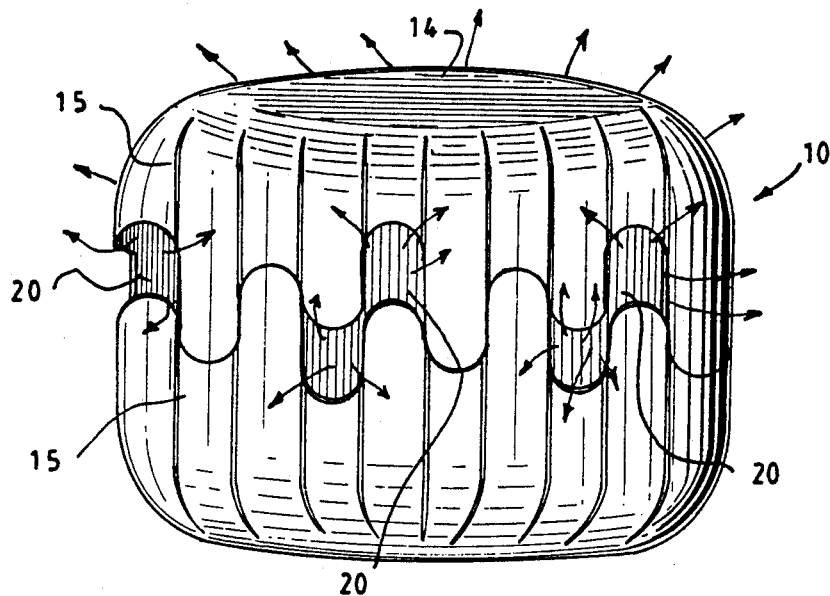
FIG. 3 is a side perspective view of the container according to the present invention illustrating the passage of ambient air through the container in an open position.

Referring in detail to FIG. 3, the container 10 is illustrated in the open position. Once again, like numerals in FIG. 3 represent the same elements as previously discussed with respect to FIGS. 1 and 2. In the open position shown, ambient air circulates through the container in the manner indicated by the arrows.

Figure 4:
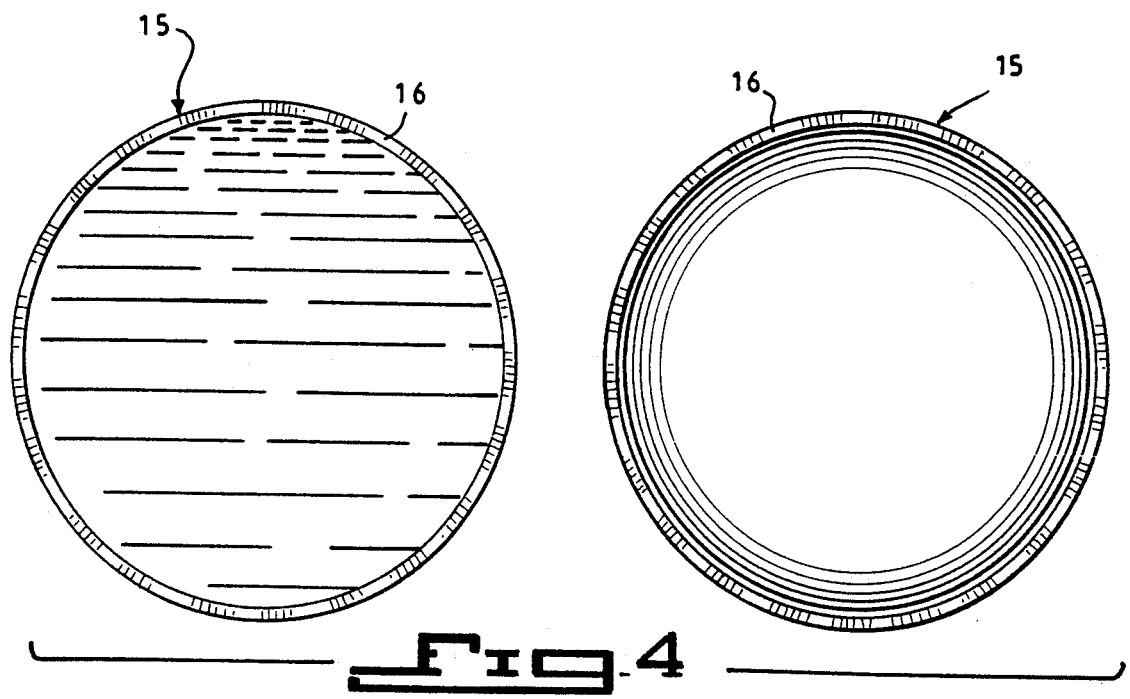
FIG. 4 is a top plan view of the top and base members of the container according to the present invention, disengaged from each other and laid side by side with their outer peripheries extending up out of the plane of the paper.

Referring in detail to FIGS. 4 and 5, in each case the container is shown with the two components taken apart and laid side by side, i.e., the top member on the left and the base member on the right. Since the periphery of the top member is curvilinear, there correctly is no indication in FIG. 4 as to where the curvilinear portions change direction or even where the changeovers back and forth from the fingers to the recesses and vice versa takes place.

The manner in which the top member seats on the base member is illustrated in dotted lines in FIG. 5 and the figure also shows how the two halves can be put together and separated.

In operation, the container is originally closed whereby the fingers and recesses of the outer peripheries of the top and base members engage each other and form a sealing engagement of the top and base members.

If one desires to open the container 10, one merely rotates the top member 11 relative to the base member 111. Such rotation causes reciprocation of the top member 11 relative to the base member 111, due to the camming interaction of the outer peripheries of top member 11 and base member 111. When the top member reciprocates away from the bottom member, the container is opened providing air passages 20 between the top member 11 and the base member 111. In the open condition, the container is activated to treat the air within the room in which it is positioned.

The outer peripheries interact to cause the top member to securely rest on the base member in a nesting configuration. Depending upon the alignment, the top member can rest on the base member in the closed, partial open or full open position. No matter how the top member is initially aligned with the base member, the top member will always rest securely on the base member because once the top member is positioned on the base member, the top member will slide downwardly onto the base member until the two members nest together. It is not possible for the top member to lean, i.e., rotate about any axis in a plane parallel to the plane of the section's upper (or in the case of the base, its lower) surface. The top section cannot slip off or strike the bottom section when being re-engaged. At most, the top member will slide down onto the base member, possibly twisting relative to the base member, but with the top and base upper and lower surfaces respectively always remaining parallel.

The outer peripheries of the top and base sections are curvilinear to avoid sharp edges and to reduce the possibility of breakage of such sharp edges, and to achieve the desired nesting and camming interaction.

The invention being thus described, it would be obvious that the same may be varied in many ways. By way of example, in the most simplified version of the invention, the camming aspects could be left out and the interfacing surfaces could be squared off or step-like configurations. The members would be moved relative to each other by lifting the top member entirely off the bottom member and rotating the top member relative to the bottom member and then repositioning the top member on the bottom member. Such variations are not to be regarded as a departure from the spirit and scope of the invention, and all such modifications as would be obvious to one skilled in the art are intended to be included within the scope of the following claims.

What is claimed is:

1. A container for an air treatment material, said container having first and second top and bottom housing sections, said housing sections each having an outer peripheral edge that is identical to and interacts with the outer peripheral edge of the other and permits the top to be laid upon the bottom in a nesting, closed configuration with the outer peripheries in engagement along their entire lengths, and the top to be rotated relative to the bottom to one or more open configurations, said outer peripheries having selected portions of their lengths which are in engagement with each other in said open positions and selected other portions of their lengths which are not in engagement with each other, but rather, spaced apart from each other, in said open positions, said other non-engaging, spaced apart portions of said outer peripheries defining air passages between, said air passages extending into the interior of said container and said air passages being closed when the container is in the closed position, said housing sections adapted to be moved reciprocally with respect to each other between said closed position and each said open position, and said housing sections being adapted to be readily separated from each other to permit replenishment of the air treatment material contained in the container.

2. A container according to claim 1, wherein said outer peripheries engage along at least three points of engagement in each of said open positions.

3. A container according to claim 1, wherein said outer peripheries are curvilinear shaped.

4. A container according to claim 1, whereby the size of the openings between the housing sections are varied in the different open positions.

5. A container according to claim 1, wherein said outer peripheries are scallop shaped.

6. A container according to claim 1, wherein said outer peripheries include camming surfaces to cause reciprocation of the top and base members relative to each other during rotation.

7. A container according to claim 1, wherein said top member and said base member are identical elements constructed from a single mold.

8. A container according to claim 1, wherein said top member and said base member include outwardly projecting outer peripheries which mate with each other so that the top member may be reciprocated outwardly from the base member thereby defining air passages therebetween and inwardly to close and seal the container.

9. A container according to claim 1, wherein said outer peripheries are curvilinear in shape so as to permit smooth rotation of the two members relative to each other and indexing of the two peripheries relative to each other to adjust the positioning of said top member relative to said base member in a plurality of positions to define different size air passages.

10. A container according to claim 1, wherein said top member is rotated relative to the base member to open the container, and during such rotation, there is a concomitant upward or vertical motion of the top member away from the base member caused by the camming interaction of the interfacing outer periphery curvilinear portions of the top and base members, and said top member is rotated further relative to the base member in order to close the container, in the same direction as it was rotated to open the container, the camming outer periphery surfaces allowing easy repositioning of the top member in nesting relation to the base member.

11. A container according to claim 1, wherein said top member is moved from the open position relative to the base member to the closed position by reversing the rotation of the top member relative to the base member until the members return to their original position of closed engagement.

12. A container according to claim 1, wherein said top member can be completely removed in order to permit replenishment of the air-treating material, and wherein the outer peripheries engage and guide further relative movement of the top member vertically downward onto the base member, until the members seat relative to each other, such that the nature of the interaction of the outer peripheries when the top member is being replaced on the base member only permits two degrees of rotational freedom, thus limiting the chances of destructive banging of the members together during replacement of the top member on the bottom member.

* * * * *

UNITED STATES PATENT AND TRADEMARK OFFICE
CERTIFICATE OF CORRECTION

PATENT NO.    : 5,265,749
DATED         : November 30, 1993
INVENTOR(S)   : Michael B. Zutler It is certified that error appears in the above-indentified patent and that said Letters Patent is hereby corrected as shown below:

In the Drawings:
At page 3, Figure 3, at the lower left section of the figure, change "15" to —115—.

At page 3, Figure 4, in the embodiment in the left-hand section of the figure, change "15" to —115—.

At page 3, Figure 4, in the embodiment in the left-hand section of the figure, change "16" to —116—.

Signed and Sealed this

Twenty-sixth Day of July, 1994

*Attest:*

BRUCE LEHMAN

*Attesting Officer*  Commissioner of Patents and Trademarks